United States Patent
Alameddine

(10) Patent No.: US 8,012,202 B2
(45) Date of Patent: Sep. 6, 2011

(54) MITRAL VALVE RING FOR TREATMENT OF MITRAL VALVE REGURGITATION

(76) Inventor: Abdallah K. Alameddine, Melrose, MA (US)

(*) Notice: Subject to any disclaimer, the term of this patent is extended or adjusted under 35 U.S.C. 154(b) by 0 days.

(21) Appl. No.: 11/190,495

(22) Filed: Jul. 27, 2005

(65) Prior Publication Data

US 2006/0025858 A1    Feb. 2, 2006

Related U.S. Application Data

(60) Provisional application No. 60/599,923, filed on Aug. 9, 2004, provisional application No. 60/591,728, filed on Jul. 27, 2004.

(51) Int. Cl.
*A61F 2/24* (2006.01)
(52) U.S. Cl. ...................... 623/2.36; 623/2.37
(58) Field of Classification Search ............... 623/2.14, 623/2.18, 2.36–2.38
See application file for complete search history.

(56) References Cited

U.S. PATENT DOCUMENTS

| | | | |
|---|---|---|---|
| 4,164,046 A * | 8/1979 | Cooley | 623/2.36 |
| 5,104,407 A * | 4/1992 | Lam et al. | 623/2.36 |
| 6,187,040 B1 * | 2/2001 | Wright | 623/2.36 |
| 6,231,602 B1 * | 5/2001 | Carpentier et al. | 623/2.36 |
| 6,368,348 B1 * | 4/2002 | Gabbay | 623/2.36 |
| 6,805,710 B2 * | 10/2004 | Bolling et al. | 623/2.36 |
| 6,955,689 B2 * | 10/2005 | Ryan et al. | 623/2.36 |
| 2001/0021874 A1 * | 9/2001 | Carpentier et al. | 623/2.37 |
| 2002/0173841 A1 * | 11/2002 | Ortiz et al. | 623/2.11 |
| 2003/0199974 A1 * | 10/2003 | Lee et al. | 623/2.36 |
| 2003/0229395 A1 | 12/2003 | Cox | |
| 2004/0167620 A1 * | 8/2004 | Ortiz et al. | 623/2.11 |
| 2005/0004668 A1 * | 1/2005 | Aklog et al. | 623/2.36 |
| 2005/0049698 A1 | 3/2005 | Bolling et al. | |
| 2005/0288776 A1 * | 12/2005 | Shaoulian et al. | 623/2.37 |
| 2006/0015178 A1 * | 1/2006 | Moaddeb et al. | 623/2.36 |
| 2006/0015179 A1 * | 1/2006 | Bulman-Fleming et al. | 623/2.36 |

OTHER PUBLICATIONS

Rackley, C. E., "Quantitative Evaluation of Left Ventricular Function by Radiographic Techniques," Circulation, 54, 862-876, Dec. 1976.

* cited by examiner

*Primary Examiner* — David Isabella
*Assistant Examiner* — Jason-Dennis Stewart
(74) *Attorney, Agent, or Firm* — Houston Eliseeva LLP

(57) ABSTRACT

An active bodily ring having a housing adapted to be sutured to a bodily component and a loop disposed in the housing, the loop capable of actively expanding and compressing during the bodily components normal function. The housing defines a first chamber and a second chamber, the first chamber containing the loop and the second chamber providing a region capable of being sutured to the bodily component. In one embodiment, the housing can be a crimped-fabric housing. In another embodiment, the housing can be a woven-fabric housing having elastic properties. The housing can be made from polyester.

11 Claims, 4 Drawing Sheets

MITRAL VALVE RING FOR TREATMENT OF MITRAL VALVE REGURGITATION

RELATED APPLICATIONS

This application claims the benefit of U.S. Provisional Application No. 60/599,923, filed on Aug. 9, 2004 and U.S. Provisional Application No. 60/591,728, filed on Jul. 27, 2004. The entire teachings of each application are herein incorporated by reference.

BACKGROUND OF THE INVENTION

Congestive heart failure is a leading cause of hospitalization and death in the United States, and its incidence is increasing. Secondary mitral regurgitation, a complication of end-stage cardiomyopathy, refers to the backflow of blood from the left ventricle to the left atrium resulting from imperfections in the mitral valve. When the mitral valve allows blood to flow backward into the left atrium, the left ventricle must pump progressively harder to circulate blood throughout the body, which in turn promotes congestive heart failure. While heart transplantation is considered a standard treatment for select patients with severe congestive heart failure and end-stage heart disease, it is only applicable to a small percentage of patients because of the small number of available donor hearts and surgical risks for weaker patients. Accordingly, alternative medical and surgical strategies are evolving to treat such conditions.

Mitral valve annuloplasty is a well known approach for treating mitral insufficiency, although other treatments are used which include replacing the mitral valve, repairing the mitral valve leaflets, and shortening or replacing the chordae tendinae. Mitral valve annuloplasty is the reparation of the mitral valve annulus which effects full closure of the leaflets by reestablishing the size and shape of the normal mitral valve annulus. Such an annuloplasty most commonly incorporates the use of a mitral annuloplasty ring wherein the ring is implanted on the mitral valve annulus.

There are three basic types of mitral annuloplasty rings used in annuloplasty procedures. They include a rigid ring, a flexible ring and a combined ring that has both a flexible component and a rigid component.

Due to their inflexibility, the rigid rings dictate the shape and contour of the mitral valve. The native mitral valve annulus flexes in response to the movement of the heart. However, with a rigid ring the annulus is not able to flex normally or move freely with the pumping action of the heart. As a result of the rigidity, the physiologic factors that normally shape the mitral valve annulus are not allowed to take precedence in shaping the valve.

Another drawback with rigid rings is that they can induce a heart condition known as systolic anterior motion in patients having a mitral valve posterior leaflet that is too "tall". During ventricular contraction, the posterior leaflet pushes the anterior leaflet in a direction opposite to the anterior leaflet's normal movement, resulting in the obstruction of the left ventricle's outflow tract.

Overall, rigid annuloplasty rings do not allow the mitral valve annulus to reestablish its normal shape and form as dictated by the action of the heart pumping. The shape and contour of the annulus are established by the inflexible shape and form of the ring itself.

Flexible rings made of polyester cloth, unlike the rigid rings, can allow the mitral valve annulus to move and flex as the heart contracts and relaxes. However, several drawbacks still exist. Proper shape and contour of the annulus is necessary in order for the mitral valve leaflets to close effectively. One shortcoming of the flexible ring is its predisposition to crimp during implantation. Crimping can be detrimental to the valve annulus, sometimes resulting in a mitral orifice that is too small. This can lead to stenosis of the valve. Furthermore, neither the flexible rings nor the combined rings can remain flexible indefinitely after annuloplasty. Since the rings are secured in place by a line of sutures attached directly to the annulus, scarring and resultant stiffening of the annulus inevitably develops. This loss of flexibility impedes the normal flexing and movement of the heart, particularly the left ventricle and, therefore, the heart cannot function optimally.

SUMMARY OF THE INVENTION

The present invention is directed toward a new active bodily ring that can be used to preserve the natural mitral valve sphincteric contraction. The active bodily ring allows the two leaflets' coaptation to remain intact and the incidence of left ventricular dysfunction will thus decrease. Also, the active bodily ring can distribute and transmit the stress evenly over the entire valve apparatus, instead of only over the anterior leaflet.

The active bodily ring includes a housing adapted to be sutured to a bodily component and a loop disposed in the housing, the loop capable of actively expanding and compressing during the bodily components normal function. The housing defines a first chamber and a second chamber, the first chamber containing the loop and the second chamber providing a region capable of being sutured to the bodily component. In one embodiment, the housing can be a crimped-fabric housing. In another embodiment, the housing can be a woven-fabric housing having elastic properties. The housing can be made from polyester.

In one embodiment, the loop can be an open-ended flat coil loop, each end adapted to substantially allow free movement of the loop within the housing. One end of the loop can include a plurality of protrusions and the other end of the loop can include a plurality of notches for engaging the protrusions thereby enabling the loop to be adjusted. The loop can provide a retraction force between about 3 and 4 Newtons when maximally stretched. The loop can be made from a material selected from a group consisting of a metal, metal alloy and polymer resin. In another embodiment, the loop can be a distensible coiled spring including a plurality loops.

A bodily component can be selected from a group consisting of a heart, a larynx, an esophagus, a trachea, a pharynx, an eyelid, a nostril, a mouth, an anus, a rectocele, a pupil, a rectum, a bladder, and a vagina. In one embodiment, the ring can be sutured to a mitral value annulus of the heart. Further, the ring can be used for a medical treatment selected from a group comprising ischemic mitral valve regurgitation, prolapse mitral valve regurgitation; mitral valve regurgitation associated with left ventricular aneurysms; mitral valve regurgitation associated dilated cardiomyopathy; and Barlow's disease.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

Figure 1A:
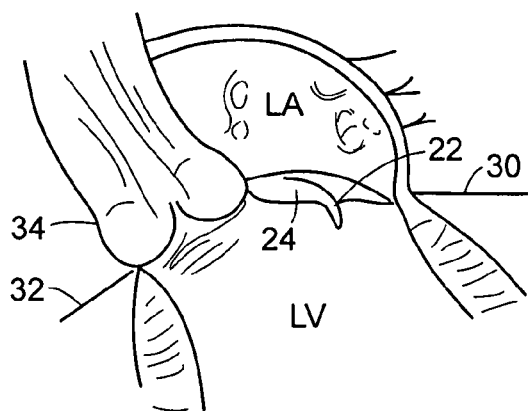
FIG. 1A is a cross-sectional view along an anterior-posterior plane through the left side of a heart illustrating healthy aortic and mitral valves and annuluses.
Figure 1B:
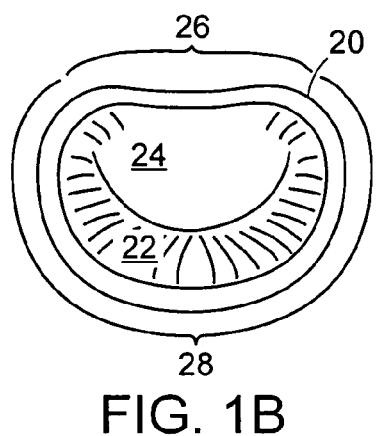
FIG. 1B is a plan view of a healthy mitral valve and annulus.

As seen in FIGS. 1A and 1B, the mitral annulus 20 represents the junction of the fibrous and muscular tissue that joins the left atrium and left ventricle. The average human mitral annular cross-sectional area is about 5-11 cm$^2$. The mitral valve is a bicuspid valve having a large posterior leaflet 22 that coapts or meets with a smaller anterior leaflet 24. The anterior aspect 26 of the annulus, which is in continuity with the fibrous skeleton of the heart, has limited flexibility, whereas the posterior aspect 28 of the annulus, which is not attached to any rigid surrounding structures, has more flexibility. For the purpose of discussion, the mitral annulus 20 (FIG. 1B) lies generally in a datum plane 30 (FIG. 1A) at an angle with respect to a second datum plane 32 in which the aortic valve 34 is generally oriented. These datum planes 30, 32 can be defined as being perpendicular to the average blood flow through the respective valves. During systole the mitral annulus 20 assumes a generally elliptical shape as shown in FIG. 1B, and is able to contract and decrease in diameter, whereas, in diastole, it assumes a more circular shape and opens to permit blood to fill the left ventricle. Annular flexibility allows for increased leaflet coaptation during systole and increased annular orifice area during diastole.

Figure 2A:
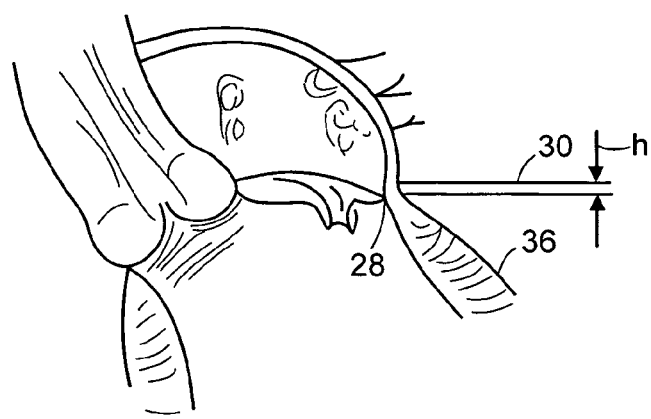
FIG. 2A is a cross-sectional view along an anterior-posterior plane through the left side of a heart illustrating a condition in the mitral valve that leads to mitral valve regurgitation.
Figure 2B:
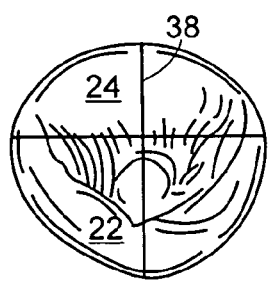
FIG. 2B is a plan view of the mitral valve of FIG. 2A.

In mitral regurgitation, dilation typically occurs along the more flexible posterior aspect 28 of the annulus, as seen in FIGS. 2A and 2B. Some patients experiencing a drop in height (h) of the posterior aspect 28 of the mitral valve annulus, as seen in FIG. 2A, and consequent relaxation of the posterior muscle wall 36 of the left ventricle. FIG. 2B illustrates the lengthening of the anterior-posterior dimension 38 and subsequent loss of coaptation between the posterior and anterior leaflets 22, 24.

Mitral regurgitation leads to a cycle of continuing volume overload of the already dilated left ventricle, progression of annular dilation, increased left ventricle wall tension, increasing degrees of mitral regurgitation and worsening congestive heart failure. In mitral regurgitation, the regurgitant volume ejected into the left atrium is dependent upon mitral orifice size, ventricular/atrial pressure gradient and heart rate. The regurgitant flow into the left atrium increases left atrial pressure, which leads to atrial enlargement and an increase in compliance, and decreases forward systemic flow. Left atrial pressures rise during systole and decline in diastole.

Figure 3:
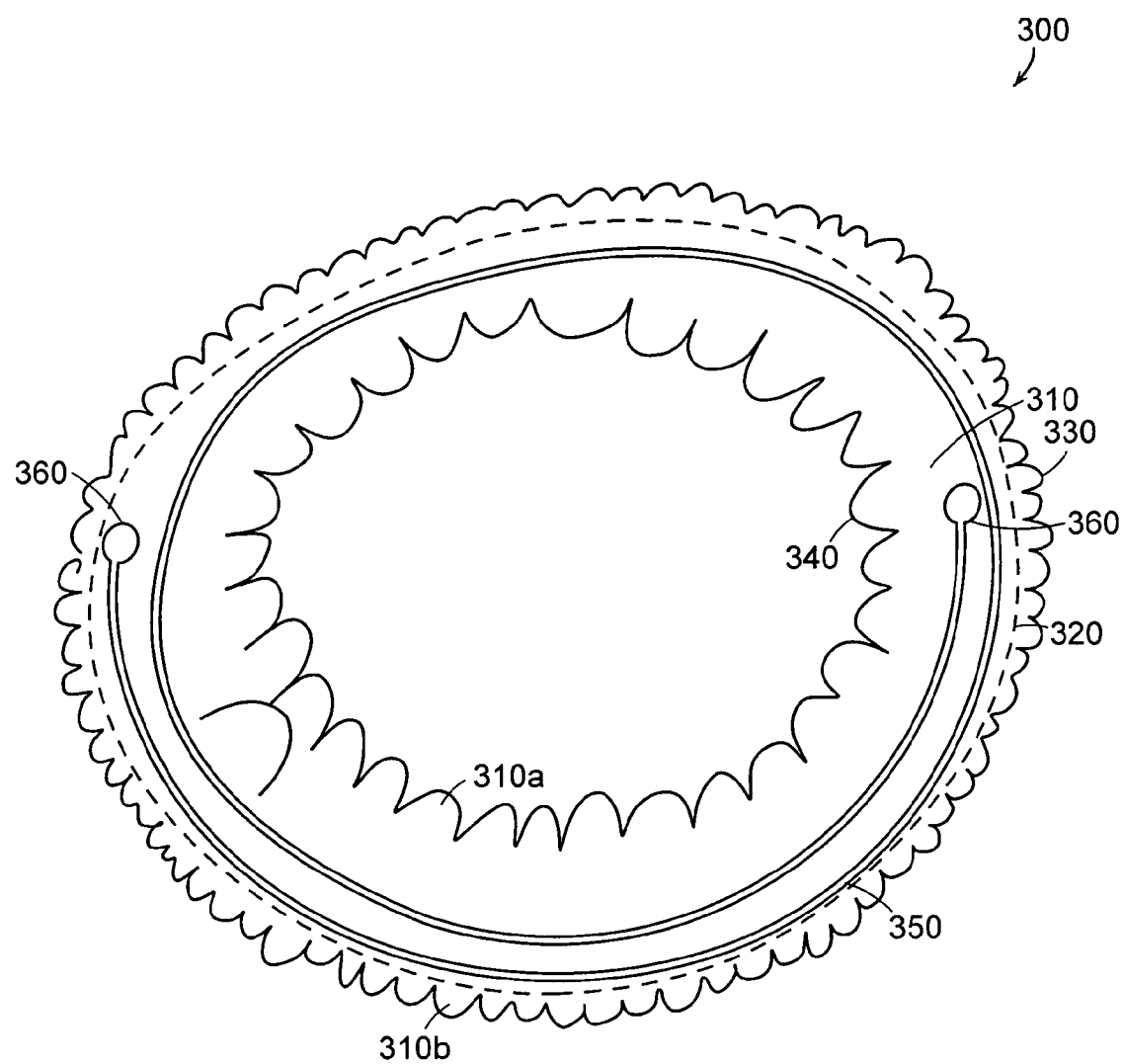
FIG. 3 is a plan view of a flat coil ring of the present invention.

FIG. 3 shows an active bodily ring 300 according to the principals of the present invention. The active bodily ring 300 includes an outer casing/housing 310 and a flat coiled loop 350. The casing 310 is divided by a seam 320 that defines an inner chamber 310a of the casing 310 and an outer chamber 310b of the casing 310. The inner chamber 310a houses the flat coiled loop 350 while the outer chamber 310b is adapted to be sutured to a bodily component, such as a mitral valve annulus 20 (FIG. 1B).

Returning to FIG. 3, the casing 310 is preferably a crimped-fabric or woven-fabric having elastic properties to allow the flat coiled loop 350 to expand and compress during the bodily component normal function. The casing 310 fabric is preferably made from DACRON® polyester from Dupont Corporation. In one embodiment, each crimp 330 of the outer circumference of the casing 310 is approximately 1.5 mm wide while each crimp 340 of the inner circumference of the casing 310 is approximately 3.0 mm.

The flat coiled loop 350 is open-ended wherein each end 360 is adapted to allow free movement of the flat coiled loop 350 within the housing while the bodily component functions. As shown, each end 360 is rounded to allow free movement, but any means known in the art can be used. The flat coiled loop 350 can preferably made from steel, a nickel-titanium alloy, also known as Nitinol, a nickel-cobalt-chromium alloy composition, sold by Elgiloy Limited Partnership under the trademark ELGILOY®, an acetal resin, sold by Dupont Corporation under the trademark DELRIN®, or any other suitable FDA approved material. The active bodily ring 300 provides an active retraction force during expansion and compression of the bodily component of which it is attached. The retraction force of the flat coiled loop 350 is between about 3 and 4 Newtons when maximally stretched.

Figure 4:
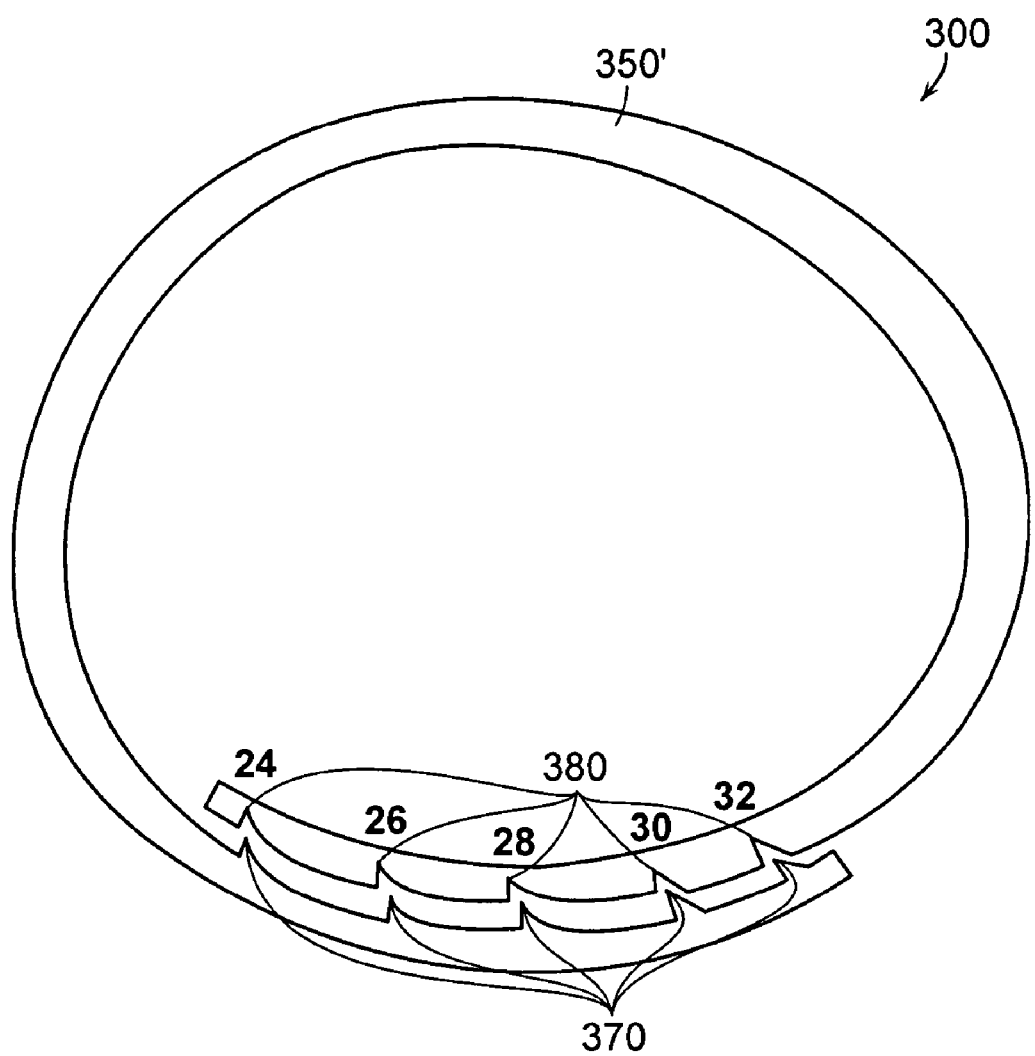
FIG. 4 is a plan view of an adjustable ring of the flat coil ring of FIG. 3.

FIG. 4 shows an optional embodiment of the flat coiled loop 350 of FIG. 3. The flat coiled loop 350' functions essentially the same as the embodiment of FIG. 3 with the exception the flat coiled loop 350' is adjustable. As such, the flat coiled loop 350' includes a plurality of protrusions 370 and notches 380 for receiving the protrusions 370 to allow the flat coiled loop 350' to be adjusted to a particular bodily component. The numbers 24, 26, 28, and 32 show the adjustable size in millimeters of the flat coiled loop 350'.

Figure 5:
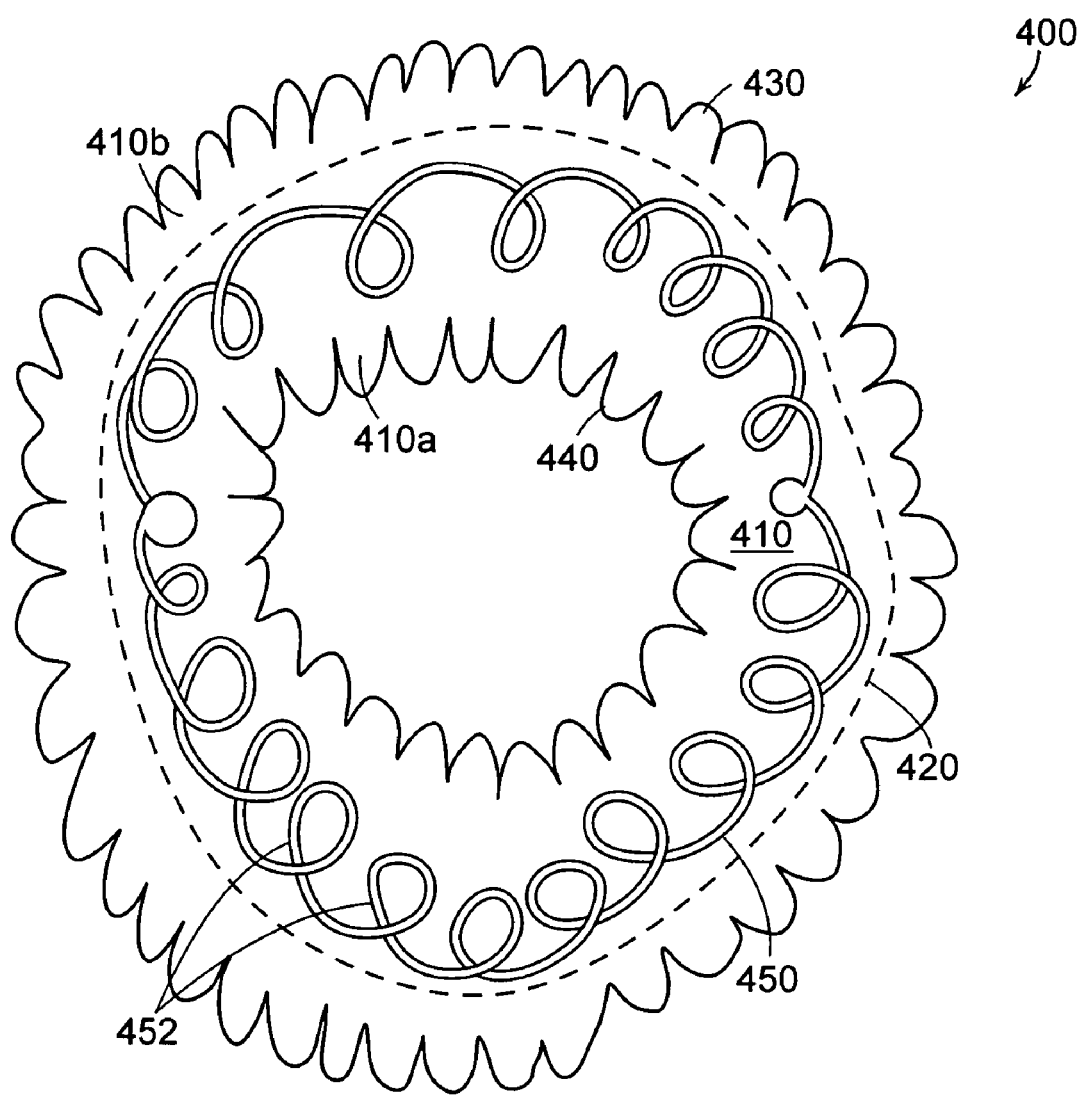
FIG. 5 is a plan view of a distensible ring of the present invention.

FIG. 5 shows another embodiment of the active bodily ring 300 of FIGS. 2 and 3. The active bodily ring 400 includes an outer casing/housing 410 and a distensible coiled spring 450. The casing 410 is divided by a seam 420 that defines an inner chamber 410a of the casing 410 and an outer chamber 410b of the casing 410. The inner chamber 410a houses the distensible coiled spring 450 while the outer chamber 410b is adapted to be sutured to a bodily component, such as a mitral valve annulus 20 (FIG. 1B).

The casing 410 is preferably a crimped-fabric or woven-fabric having elastic properties to allow the distensible coiled spring 450 to expand and compress during the bodily component normal function. The casing 410 fabric is preferably made from DACRON® polyester. In one embodiment, each crimp 430 of the outer circumference of the casing 410 is approximately 1.5 mm while each crimp 440 of the inner circumference of the casing 410 is approximately 3.0 mm.

The distensible coiled spring 450 is close-ended and includes a plurality of loops 452 to allow expansion and compression during bodily component normal function. For mitral valve treatment, the distensible coiled spring 450 can be soft and pliable when stretched and relaxed, thus it preserves maximum coaptation of the leaflets of a mitral valve. Further, the distensible coiled spring 450 assures effective transfer of the pressure stresses from the left ventricular to the annulus as well as to the left atrium.

Either active bodily ring 300 or active bodily ring 400 can be used for a wide range of bodily components. Some of the bodily components include a heart, a larynx, an esophagus, a trachea, a pharynx, an eyelid, a nostril, a mouth, an anus, a rectocele, a pupil, a rectum, a bladder, and a vagina. Medical treatment associated with the repair of the heart can include ischemic mitral valve regurgitation, prolapse mitral valve regurgitation, mitral valve regurgitation associated with left ventricular aneurysms, mitral valve regurgitation associated dilated cardiomyopathy, and Barlow's disease.

Either active bodily ring 300 or active bodily ring 400 can be used to treat mitral valve regurgitation since each design lowers energy expenditure of the ventricle by actively moving the annulus, whereas prior art designs are passively moving the annulus. The 10 to 20 year survival with the standard (prior art), non-coiled, non-springed ring is around 85%. However, the 80-90 percent effectiveness is with the assumption that the surgeon successfully installs the prior art ring. The initial success rate for mitral repair (non-ischemic) approaches no more than 75%. However, the active bodily ring 300 or active bodily ring 400 allows for much easier insertion and therefore the success rate can be higher. Because the active bodily ring 300 or active bodily ring 400 are active in nature, the simulation of the natural movement of the annulus allows easier completion of the repair.

The active bodily ring 300 has the most clinical impact in ischemic type of mitral regurgitation. In the ischemic patient, the ventricle needs all the assistance it can get, as the five-year survival rate approximate 50%. The loop 350 helps the ventricular contractility to be transmitted harmoniously across with less energy expenditure than the standard prior art rings. Thus, the ventricular strain can be improved.

The following active bodily ring 300 parameters are for a mitral valve ring:

Perimeter=10 cm for a 26-24 mm ring;
Normal mitral valve diameter shortening (commissure to commissure) between systole and diastole=~10 mm;
Circular perimeter shortening of mitral valve=$(2\pi r)$=~3 cm;
Number of sutures=12; wherein each suture comprises two crimps' length (3 mm/crimp);
Length of crimped polyester knit fabric cover/casing 310 for the sutures=7 cm (~12×6 mm each);
Remaining un-sutured length of crimped fabric cover/casing 310=11 intervals (1 interval=3 mm) at ~33 mm total;
Size of each inner crimp 320 on the inner cover=~3 mm;
Outer edge to inner edge length=~4 mm;
Outer edge crimps=~1 mm each;
Height of inner crimp edge=~3 mm; and
Outer crimps 330=~1.5 mm each.

The active bodily ring 400 is well suited for mitral valve regurgitation when restoring left ventricular aneurysms or dilated cardiomyopathy. For treatment of mitral regurgitation associated with left ventricular aneurysms, the dynamic nature of the distensible coiled spring 450 ensures much greater ventricle efficiency than standard prior art non-dynamic rings. This advantage ensures a higher ten-year survival rate in this group of patients (presently at 25%). The number of loops 452 of the distensible coiled spring 450 can be decreased according to the level of severity of ventricular dysfunction. Therefore, there are two sub-types of the active bodily ring 400.

One sub-type is for severe left-ventricular dysfunction (4+ mitral regurgitation). In this situation, a smaller number of loops 452 are needed. The other sub-type is for less severe left-ventricular dysfunction (3+ mitral regurgitation). In this situation, a greater number of loops 452 are needed.

The active bodily ring 400 provides the following advantages: 1) dynamic reduction of the posterior annulus in systole; 2) effective distribution of left ventricular force during systole; 3) preservation of the physiologic saddle conformation of mitral annulus; 4) avoids late paravalvular leaks because of absence of abnormal retraction between healing tissues and the sewing ring; 5) maintains left ventricular and left atrial geometry and functions; and 6) mimics the corrugation of collagen bundles of the mitral valve because of its dynamic geometry and the orientation of its loops. Further, the active bodily ring 400 improves survival rates because it provides: 1) decreased in subsequent myocardial decompensation and failure; 2) decreased myocardial oxygen demand; and 3) decreased transmural wall tension.

While this invention has been particularly shown and described with references to preferred embodiments thereof, it will be understood by those skilled in the art that various changes in form and details may be made therein without departing from the scope of the invention encompassed by the appended claims.

What is claimed is:

1. An active bodily ring, comprising:
   a circular shaped housing fabricated from a crimpled fabric adapted to be sutured to a mitral valve annulus of a heart; and
   an open-ended loop disposed in the housing and having the form of a flat coiled loop with one end radially inward, forming an arc length defined by an angle of 540 degrees about a circumference of the housing with each end adapted to substantially allow free movement of the loop within the housing and flexing allowing expansion and compression of the loop during normal function of the heart,
   wherein the ends are rounded to facilitate the free movement.

2. The active bodily ring of claim 1, wherein the housing defines a first chamber and a second chamber, the first chamber containing the loop and the second chamber providing a region capable of being sutured to the mitral value annulus.

3. The active bodily ring of claim 1, wherein the housing is a woven-fabric housing having elastic properties.

4. The active bodily ring of claim 1, wherein the fabric includes polyester.

5. The active bodily ring of claim 1, wherein the loop provides a retraction force between 3 and 4 Newtons when maximally stretched.

6. The active bodily ring of claim 1, wherein the loop is made from a material selected from a group consisting of a metal, a metal alloy, and a polymer resin.

7. The active bodily ring of claim 1, wherein the ring is used for a medical treatment selected from the group comprising ischemic mitral valve regurgitation, prolapse mitral valve regurgitation, mitral valve regurgitation associated with left ventricular aneurysms, mitral valve regurgitation associated dilated cardiomyopathy, and Barlow's disease.

8. A method of repairing a mitral valve of a heart, comprising:
   disposing a loop in a circular shaped housing, said loop capable of actively expanding and compressing during normal function of the mitral valve of the heart, wherein the loop is an open-ended flat coiled loop, having one end radially inward, said loop forming an arc length defined by an angle of 540 degrees around a circumference of the housing, each end rounded to substantially allow free movement of the loop within the housing; and
   suturing the housing to a mitral valve annulus of the mitral valve of the heart.

9. The method of claim 8, wherein the housing defines a first chamber and a second chamber, the first chamber containing the loop and the second chamber providing a region capable of being sutured to the mitral valve annulus.

10. The method of claim 8, wherein the ring is used for a treatment selected from a group consisting of ischemic mitral valve regurgitation, prolapse mitral valve regurgitation, mitral valve regurgitation associated with left ventricular aneurysms, mitral valve regurgitation associated dilated cardiomyopathy, and Barlow's disease.

11. The method of claim 8, further comprising the loop providing a retraction force between 3 and 4 Newtons.

* * * * *